United States Patent
Chong

(10) Patent No.: US 9,993,153 B2
(45) Date of Patent: Jun. 12, 2018

(54) OPTICAL COHERENCE TOMOGRAPHY SYSTEM AND METHOD WITH MULTIPLE APERTURES

(71) Applicant: SANTEC CORPORATION, Komaki, Aichi (JP)

(72) Inventor: Changho Chong, Los Altos, CA (US)

(73) Assignee: SANTEC CORPORATION, Komaki, Aichi (JP)

( * ) Notice: Subject to any disclaimer, the term of this patent is extended or adjusted under 35 U.S.C. 154(b) by 0 days. days.

(21) Appl. No.: 15/202,925

(22) Filed: Jul. 6, 2016

(65) Prior Publication Data
US 2018/0008143 A1    Jan. 11, 2018

(51) Int. Cl.
| A61B 3/14 | (2006.01) |
| A61B 3/10 | (2006.01) |
| A61B 3/15 | (2006.01) |
| G02B 27/14 | (2006.01) |
| G02B 27/28 | (2006.01) |
| G02B 26/08 | (2006.01) |
| A61B 3/00 | (2006.01) |
| G01B 9/02 | (2006.01) |

(52) U.S. Cl.
CPC .......... *A61B 3/102* (2013.01); *A61B 3/0025* (2013.01); *A61B 3/0041* (2013.01); *A61B 3/0091* (2013.01); *A61B 3/152* (2013.01); *G01B 9/02091* (2013.01); *G02B 26/0816* (2013.01); *G02B 27/141* (2013.01); *G02B 27/283* (2013.01)

(58) Field of Classification Search
CPC ..... A61B 3/102; A61B 3/0025; A61B 3/0041; A61B 3/0091; A61B 3/152; G02B 27/141; G02B 26/0816
USPC ................................ 351/206, 205, 200, 208
See application file for complete search history.

(56) References Cited

U.S. PATENT DOCUMENTS

| 4,466,699 A | 8/1984 | Droessler et al. |
| 5,022,745 A | 6/1991 | Zayhowski et al. |

(Continued)

FOREIGN PATENT DOCUMENTS

| DE | 10 2011 114 797 A1 | 4/2013 |
| JP | 2006-202543 A | 8/2006 |

(Continued)

OTHER PUBLICATIONS

Jeong et al., "Spectral-domain OCT with dual illumination and interlaced detection for simultaneous anterior segment and retina imaging," Optics Express, vol. 20, Issue 17, pp. 19148-19159 (2012).

(Continued)

*Primary Examiner* — Tuyen Tra
(74) *Attorney, Agent, or Firm* — Foley & Lardner LLP

(57) ABSTRACT

An optical coherence tomography (OCT) system using partial mirrors is generally described. In an example, the OCT system includes a swept light source. The system further includes an interferometer into which light from the light source is directed and a detector configured to produce an imaging sample signal based on light received from the interferometer. The system also includes a partial mirror disposed over an aperture, wherein the partial mirror is configured to transmit light within a first wavelength range and reflect light within a second wavelength range.

17 Claims, 10 Drawing Sheets

(56) References Cited

U.S. PATENT DOCUMENTS

| | | | |
|---|---|---|---|
| 5,319,668 | A | 6/1994 | Luecke |
| 5,372,135 | A | 12/1994 | Mendelson et al. |
| 5,430,574 | A | 7/1995 | Tehrani |
| 5,537,162 | A * | 7/1996 | Hellmuth ............... A61B 3/102 351/206 |
| 5,561,523 | A | 10/1996 | Blomberg et al. |
| 5,982,963 | A | 11/1999 | Feng et al. |
| 6,111,645 | A | 8/2000 | Tearney et al. |
| 6,134,003 | A | 10/2000 | Tearney et al. |
| 6,160,826 | A | 12/2000 | Swanson et al. |
| 6,275,718 | B1 | 8/2001 | Lempert |
| 6,282,011 | B1 | 8/2001 | Tearney et al. |
| 6,373,632 | B1 | 4/2002 | Flanders |
| 6,421,164 | B2 | 7/2002 | Tearney et al. |
| 6,485,413 | B1 | 11/2002 | Boppart et al. |
| 6,501,551 | B1 | 12/2002 | Tearney et al. |
| 6,564,087 | B1 | 5/2003 | Pitris et al. |
| 7,099,358 | B1 | 8/2006 | Chong |
| 7,231,243 | B2 | 6/2007 | Tearney et al. |
| 7,323,680 | B2 | 1/2008 | Chong |
| 7,324,214 | B2 | 1/2008 | De Groot et al. |
| 7,352,783 | B2 | 4/2008 | Chong |
| 7,382,809 | B2 | 6/2008 | Chong et al. |
| 7,388,891 | B2 | 6/2008 | Uehara et al. |
| 7,400,410 | B2 | 7/2008 | Baker et al. |
| 7,414,779 | B2 | 8/2008 | Huber et al. |
| 7,428,057 | B2 | 9/2008 | De Lega et al. |
| 7,489,713 | B2 | 2/2009 | Chong et al. |
| 7,701,588 | B2 | 4/2010 | Chong |
| 7,725,169 | B2 | 5/2010 | Boppart et al. |
| 7,835,010 | B2 | 11/2010 | Morosawa et al. |
| 7,865,231 | B2 | 1/2011 | Tearney et al. |
| 7,869,057 | B2 | 1/2011 | De Groot |
| 7,884,945 | B2 | 2/2011 | Srinivasan et al. |
| 7,961,312 | B2 | 6/2011 | Lipson et al. |
| 8,036,727 | B2 | 10/2011 | Schurman et al. |
| 8,115,934 | B2 | 2/2012 | Boppart et al. |
| 8,315,282 | B2 | 11/2012 | Huber et al. |
| 8,405,834 | B2 | 3/2013 | Srinivasan et al. |
| 8,500,279 | B2 | 8/2013 | Everett et al. |
| 8,625,104 | B2 | 1/2014 | Izatt et al. |
| 8,690,328 | B1 | 4/2014 | Chong |
| 8,690,330 | B2 | 4/2014 | Hacker et al. |
| 9,163,930 | B2 * | 10/2015 | Buckland |
| 2002/0163948 | A1 | 11/2002 | Yoshida et al. |
| 2005/0171438 | A1 | 8/2005 | Chen et al. |
| 2005/0201432 | A1 | 9/2005 | Uehara et al. |
| 2005/0213103 | A1 | 9/2005 | Everett et al. |
| 2006/0105209 | A1 | 5/2006 | Thyroff et al. |
| 2006/0109872 | A1 | 5/2006 | Sanders |
| 2006/0215713 | A1 | 9/2006 | Flanders et al. |
| 2007/0040033 | A1 | 2/2007 | Rosenberg |
| 2007/0076217 | A1 | 4/2007 | Baker et al. |
| 2007/0081166 | A1 | 4/2007 | Brown et al. |
| 2007/0133647 | A1 | 6/2007 | Daiber |
| 2007/0141418 | A1 | 6/2007 | Ota et al. |
| 2007/0291277 | A1 | 12/2007 | Everett et al. |
| 2008/0269575 | A1 | 10/2008 | Iddan |
| 2009/0022181 | A1 | 1/2009 | Atkins et al. |
| 2009/0103050 | A1 | 4/2009 | Michaels et al. |
| 2009/0169928 | A1 | 7/2009 | Nishimura et al. |
| 2009/0268020 | A1 * | 10/2009 | Buckland ............... A61B 3/102 348/78 |
| 2009/0290613 | A1 | 11/2009 | Zheng et al. |
| 2010/0157308 | A1 | 6/2010 | Xie |
| 2010/0246612 | A1 | 9/2010 | Shimizu |
| 2010/0284021 | A1 | 11/2010 | Hacker |
| 2011/0235045 | A1 | 9/2011 | Koerner |
| 2011/0255054 | A1 | 10/2011 | Hacker et al. |
| 2011/0299034 | A1 | 12/2011 | Walsh et al. |
| 2012/0026466 | A1 | 2/2012 | Zhou et al. |
| 2012/0136259 | A1 | 5/2012 | Milner et al. |
| 2012/0188555 | A1 | 7/2012 | Izatt et al. |
| 2014/0051952 | A1 | 2/2014 | Reichgott et al. |
| 2014/0111774 | A1 | 4/2014 | Komine |
| 2014/0228681 | A1 | 8/2014 | Jia et al. |
| 2015/0348287 | A1 | 12/2015 | Yi et al. |

FOREIGN PATENT DOCUMENTS

| | | |
|---|---|---|
| JP | 2008-188047 | 8/2008 |
| JP | 2010-172538 | 8/2010 |
| WO | WO-2012/075126 A2 | 6/2012 |
| WO | WO-2013/168149 A1 | 11/2013 |
| WO | WO-2015/121756 A2 | 8/2015 |

OTHER PUBLICATIONS

Changho Chong, et al. "Large Coherence Length Swept Source for Axial Length Measurement of the Eye." Applied Optics 48:10 (2009): D145-150.

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

Dai et al., "Optical coherence tomography for whole eye segment imaging," Optics Express, vol. 20, No. 6 (2012) pp. 6109-6115.

Dhalla et al., "Simultaneous swept source optical coherence tomography of the anterior segment and retina using coherence revival," Optics Letters, vol. 37 No. 11, Jun. 1, 2012, pp. 1883-1885.

English Translation of the International Search Report and Written Opinion on International Application No. PCT/EP2009/009189, dated Apr. 6, 2010, 12 pages.

F. Lexer et al., "Wavelength-tuning interferometry of intraocular distances," Applied Optics, vol. 36, No. 25, pp. 6548-53 (Sep. 1, 1997).

Fainman, Y. et al., "Nanophotonics for Information Systems," Information Optics and Photonics (T. Fournel and B. Javidi eds., Springer New York, 2010) pp. 13-37.

International Preliminary Report on Patentability in corresponding international application No. PCT/US2015/019299 dated Sep. 22, 2016.

International Preliminary Report on Patentability in corresponding international application No. PCT/US2015/032727 dated Dec. 8, 2016.

International Preliminary Report on Patentability in International Application No. PCT/IB2015/000808.

International Search Report and Written Opinion dated Aug. 26, 2015 for PCT/US15/32727 (8 pages).

International Search Report and Written Opinion in corresponding application No. PCT/US2016/035012 dated Aug. 18, 2016.

International Search Report and Written Opinion in International Application No. PCT/US2015/19299 dated Nov. 2, 2015 (10 pages).

International Search Report and Written Opinion in PCT/IB2015/000808 dated Oct. 20, 2015 (12 pages).

Jia et al., Split-Spectrum Amplitude-Decorrelation Angiography with Optical Coherence Tomography, Optics Express, vol. 20 No. 4, Feb. 9, 2012, pp. 4710-4725.

Lexer et al., "Wavelength-tuning interferometry of intraocular distances", Applied Optics, vol. 36, No. 25, Sep. 1, 1997, pp. 6548-6553.

Mariampillai et al., Speckle Variance Detection of Microvasculature Using Swept-Source Optical Coherence Tomography, Optics Letters, vol. 33 No. 13, Jul. 1, 2008, pp. 1530-1532.

Nankivil et al., Handheld, rapidly switchable, anterior/posterior segment swept source optical coherence tomography probe, OSA Nov. 1, 2015; vol. 6, No. 11; DOI:10.1364/BOE.6.004516; Biomedical Optics Express 4516-4528.

P. Tayebati et al., "Microelectromechanical tunable filter with stable half symmetric cavity," Electronics Letters, vol. 34, No. 20, pp. 1967-68 (Oct. 1, 1998).

Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.

Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.

(56) References Cited

OTHER PUBLICATIONS

Sergie Ortiz, et al. "Corneal Topography From Spectral Optical Coherence Tomography (SOCT)." Biomedical Optics Express 2:12, (2011):3232-3247.
U.S. Notice of Allowance on 105093-0102 dated Dec. 6, 2013.
U.S. Notice of Allowance on U.S. Appl. No. 14/601,945 dated Sep. 13, 2016.
U.S. Notice of Allowance on U.S. Appl. No. 14/613,644 dated Nov. 7, 2016.
U.S. Notice of Allowance on U.S. Appl. No. 14/613,644 dated Nov. 18, 2016.
U.S. Notice of Allowance on U.S. Appl. No. 14/641,200 dated Jul. 12, 2016.
U.S. Office Action on 105093-0102 dated Sep. 12, 2013.
U.S. Office Action on 105093-0116 dated Aug. 19, 2015.
U.S. Office Action on U.S. Appl. No. 14/601,945 dated Mar. 2, 2016.
U.S. Office Action on U.S. Appl. No. 14/613,644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Nov. 18, 2016.
U.S. Office Action on U.S. Appl. No. 14/723,325 dated Apr. 24, 2017.
US Office Action on U.S. Appl. No. 15/630,654 dated Apr. 4, 2018.

* cited by examiner

OPTICAL COHERENCE TOMOGRAPHY SYSTEM AND METHOD WITH MULTIPLE APERTURES

BACKGROUND

The following description is provided to assist the understanding of the reader. None of the information provided or references cited is admitted to be prior art.

Optical coherence tomography (OCT) is an imaging technique often used in a medical setting. OCT systems are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The correct alignment of the sample ensures that the correct portion of the sample is being imaged and that the resolution of that image is maximized. In many OCT systems, the sample is often aligned to the system by mechanical movement of the OCT system which requires complex and large, space consuming components.

SUMMARY

In an embodiment, the present technology provides an improved optical coherence tomography (OCT) system capable, for example, of allowing patients to align their own eye to the system. In an illustrative embodiment, the OCT system includes a light source configured to emit a light beam. The system further includes an interferometer that is configured to split the light beam into a reference beam and a sample beam. The system further includes a mirror system that configured to route the sample beam to a first aperture for imaging of a sample.

In some embodiments, the sample may be a patients eye. The system may also include a first partial mirror positioned across at least a portion of the first aperture. The partial mirror is configured to transmit light within a first wavelength range and reflect light within a second wavelength range. For example, the partial mirror may transmit light at infrared wavelengths, and reflect light at visible wavelengths. The system further includes a detector that is configured to detect a signal based on interference between the reference beam and a portion of the sample beam reflected from the sample.

In additional embodiments of the system, the system includes a second aperture for imaging, wherein the mirror system further comprises a switching mirror configured to selectively direct at least a portion of the sample beam into the first aperture or direct at least a portion of the sample beam towards the second aperture. The second aperture may include a second partial mirror positioned across at least a portion of the second aperture or the first partial mirror may be positioned across at least a portion of each of the first and second apertures. In some embodiments, the switching mirror includes a polarized beam splitter configured to direct light having a first polarization direction toward the first aperture and to direct light having a second polarization direction toward the second aperture. Alternatively, the switching mirror includes an actuator configured to selectively move the switching mirror into and out of a sample path to selectively direct the sample beam toward the first aperture or the second aperture. In other embodiments, the system includes a fixation mark etched on the partial mirror, wherein the fixation mark is aligned with an optical axis along which the sample beam is configured to pass through the first aperture. In other embodiments, the system includes a fixation light that is positioned behind the partial mirror, wherein the fixation light is configured to emit a beam of light along an optical axis along which the sample beam is configured to pass through the first aperture.

The system may also include an eye cup that is disposed over the first aperture. In some embodiments, the first partial mirror has an anti-reflection coating. In an embodiment, the anti-reflection coating is disposed only on one side of the mirror. In an embodiment, the system includes a display integrated into the first partial mirror, wherein the display is configured to present measured diagnostic information based on the detected signal. In yet another embodiment, the system includes a distance sensor configured to sense a distance of the sample from the first aperture, and an alarm configured to indicate when the distance is within a range suitable for conducting a measurement with the OCT system.

A method of using an optical coherence tomography (OCT) system is also discloses in accordance with an illustrative embodiment. The method includes emitting a beam from a light source and splitting the beam into a reference beam and a sample beam at an interferometer. The method further includes directing, via a mirror system, the sample beam through a first aperture and through a partial mirror that is disposed over at least a portion of the first aperture. The partial mirror is configured to transmit light within a first wavelength range and reflect light within a second wavelength range. For example, the partial mirror may transmit all light at an infrared wavelength and reflect all light at a visible wavelength. The method also includes directing, via the mirror system, a portion of the sample beam reflected from a sample to a detector and comparing, via the detector, the reference beam with the portion of the sample beam reflected from the sample to generate a measurement signal corresponding to the sample.

In some embodiments, the mirror system includes a switching mirror configured to selectively direct the sample beam toward the first aperture or toward a second aperture. In an embodiment, the switching mirror includes a polarized beam splitter, the method further comprises directing, by the polarized beam splitter, the sample beam toward either the first aperture or the second aperture based on a polarization direction of the sample beam, wherein light having a first polarization direction is directed toward the first aperture and light having a second polarization is directed toward the second aperture, and wherein the first polarization direction is perpendicular to the second polarization direction. In other embodiments, the method further includes moving, via an actuator, the switching mirror into and out of a path of the sample beam. The switching mirror is configured to direct light to the second aperture when the switching mirror is located within the path of the sample beam, and the sample beam passes to the first aperture when the switching mirror is not located within the path of the sample beam.

In an embodiment, a method using an optical coherence tomography (OCT) system is disclosed in which a patient aligns his or her eye with a first aperture by using a reflection in a partial mirror. The partial mirror is disposed over at least a portion of the first aperture and is configured to pass infrared light and reflect visible light. The patient's eye receives a sample beam that passes through the first aperture and the partial mirror and is reflected back into the OCT system. The OCT system may perform a measurement of the eye is based on the reflected sample beam.

In some embodiments, the alignment of the eye with the first aperture includes aligning the eye with a fixation light emitted through the first aperture, wherein the fixation light is disposed along an optical axis of the sample beam. In other embodiments, the alignment of the eye is the first aperture includes aligning the eye with a fixation mark disposed on the partial mirror, wherein the fixation mark is disposed along an optical axis of the sample beam.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
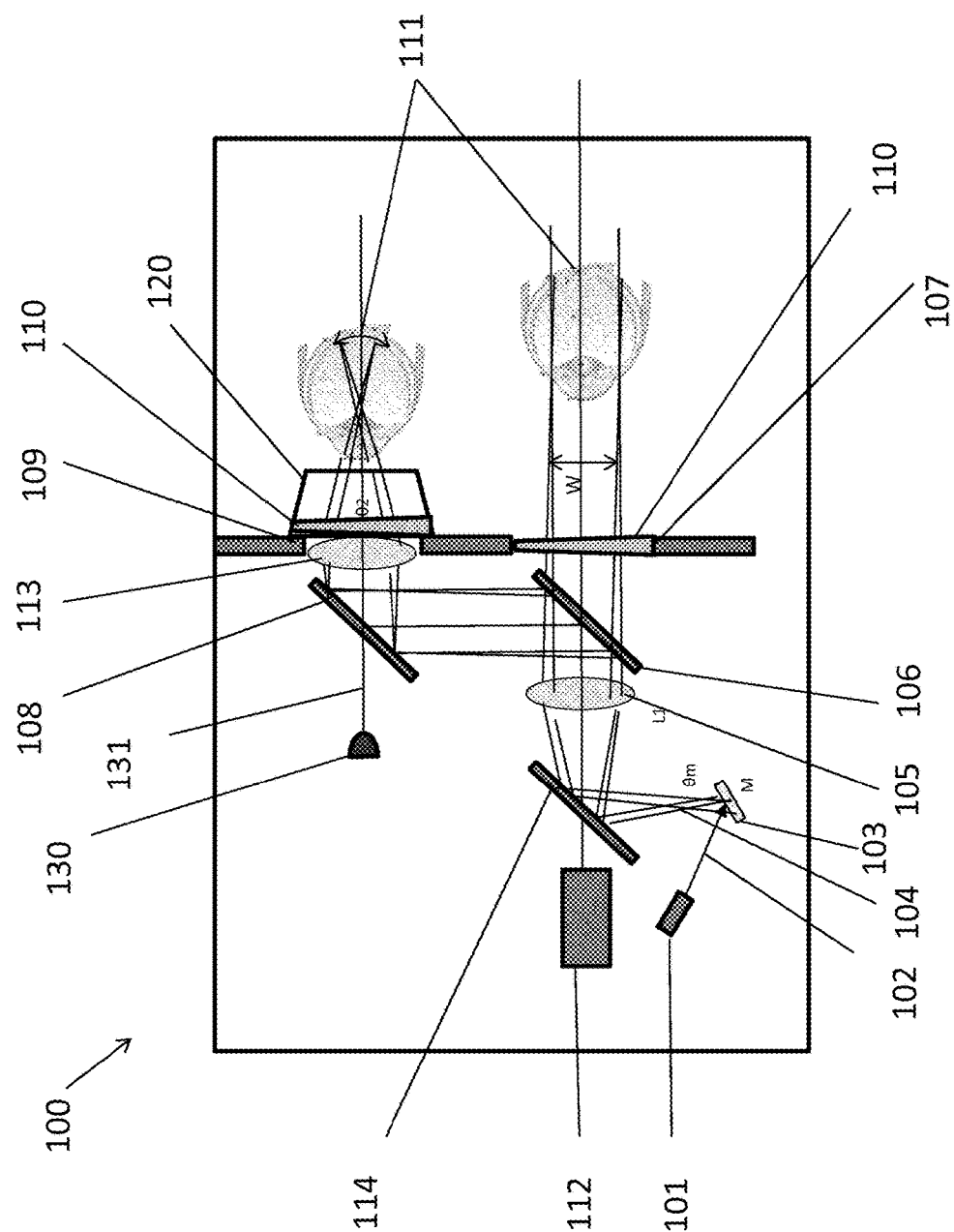
FIG. 1 depicts a representation of an optical coherence tomography (OCT) system in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system that utilizes at least one partial mirror and at least one fixation point that allow a patient to align his or her eye to the system. The OCT system may be additionally configured to have multiple different apertures configured to facilitate imaging of different portions of a sample In an OCT device designed to image an eye, it is desirable to provide the capability for imaging multiple portions of the eye, including for example the anterior chamber, the retina, the whole eye, etc. In order to image these separate portions of the eye, the angle of incidence of an incoming sample beam must be different. That is, for an anterior chamber or whole eye scan, it is desirable to have a direct angle of incidence to the eye. Whereas, for a retinal scan, it is desirable to have a converging angle of incidence where the focal point is inside of the eye. To accomplish each of these diverse imaging goals, a system of lenses and mirrors is provided that can change the sample beam's optical path and that facilitates alignment of the patient's eye with an appropriate imaging axis.

Generally, previous optical coherence tomography (OCT) devices have utilized a singular aperture. See, e.g., "Spectral-domain OCT with dual illumination and interlaced detection for simultaneous anterior segment and retina imaging," Jeong et al., Optics Express, Vol. 20, Issue 17, pp. 19148-19159 (2012). This constraint limits the device to either one type of scan, or requires a large space to accommodate many complex adjustable optic lenses and mirrors. Such complex configurations have many moving parts and may not efficiently measure the eye with the best possible resolution. Furthermore, these devices have required mechanical or joystick alignment of the system relative to the patient's eye. As a result, such systems have been large, mechanically complex, and difficult to align to a patient's eye. The methods and systems disclosed herein advantageously reduce the number of complex components utilized in multiple image range OCT devices, and allow for a more efficient means of aligning the eye to the OCT system. For example, the systems and methods disclosed herein allow a patient to align his or her own eye to the OCT system by using a fixation point and a partial mirror.

In addition, methods and systems disclosed herein advantageously utilize two separate apertures that each facilitate imaging of different portions of a sample. The use of two separate apertures effectively reduces the number of complex moving parts and also reduces the overall size of the OCT system. The methods and systems disclosed below allow for a smaller size, quicker eye-system alignment, and at least two different types of scans.

FIG. 1 depicts an optical coherence tomography (OCT) system 100 in accordance with an illustrative embodiment. In alternative embodiments, some elements may be modified, added, or omitted. The OCT system 100 includes at least one swept light source (not pictured) and an interferometer (also not pictured). The swept light source(s) emit at least one beam 102. In other embodiments there may be more than one beam with each beam having a unique frequency and wavelength. The beam is passed through the interferometer (not pictured) and directed to a scanner mirror 103 via a collimating lens 101. The scanner mirror 103 changes the path of the light and emits the beam 102 into a sample path, also known as the sample beam 104.

The scanner mirror 103 is a mirror that can change the path of the beam 102 into a range of different paths known as the sample beam 104. In some embodiments, the scanner mirror 103 is configured to be a pivoted mirror that can be actuated and rotated in order to achieve the desired sample beam 104 range. In other embodiments, the scanner mirror 103 may be an electronically controlled refractor. The scanner mirror 103 is not limited to either of these embodiments.

Figure 2:
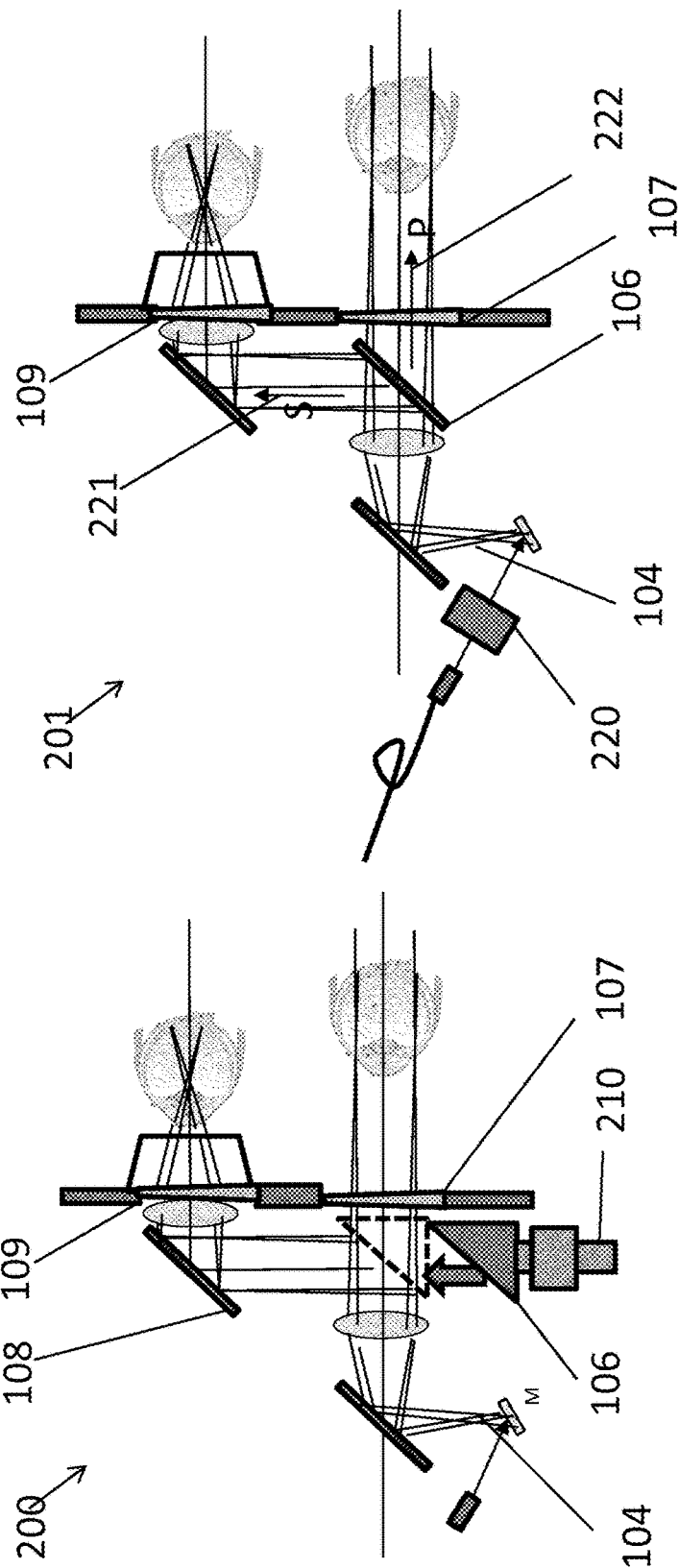
FIG. 2a depicts a representation of an optical coherence tomography (OCT) system in which an actuated switching mirror controls which aperture receives a sample beam in accordance with an illustrative embodiment.
FIG. 2b depicts a representation of an optical coherence tomography (OCT) system in which a partial beam splitter is used as a switching mirror in accordance with an illustrative embodiment.

The sample beam 104 is then reflected off a mirror 114 through a lens 105 to a switching mirror 106. The switching mirror 106 allows the sample beam 104 to either continue into a first scan aperture 107 or reflects the sample beam 104 to a third mirror 108 that is configured to reflect the beam into a second scan aperture 109. In an embodiment, the first scan aperture 107 is configured for anterior and/or whole eye imaging and the second scan aperture 109 is configured for retinal imaging. In some embodiments, the switching mirror 106 may be a mirror that is actuated by a solenoid, as illustrated in FIG. 2a and discussed in additional detail below. In other embodiments, the switching mirror 106 may be a partial beam splitter, as illustrated in FIG. 2b and discussed in additional detail below.

Figure 3:
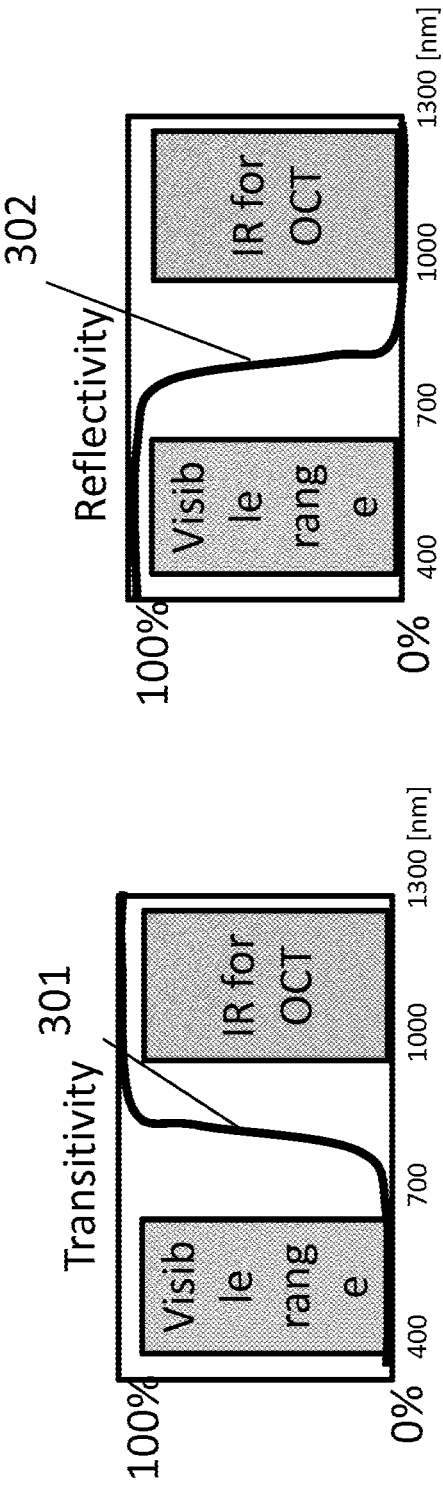
FIG. 3a depicts a representation of the transitivity properties of a partial mirror in accordance with an illustrative embodiment.
FIG. 3b depicts a representation of the reflectivity properties of a partial mirror in accordance with an illustrative embodiment.

If the sample beam 104 is not completely reflected by the switching mirror 106, at least a portion of the sample beam 104 may enter into the first scan aperture 107. The first scan aperture 107 includes a partial mirror 110. In an embodiment, the partial mirror 110 transmits most or all infrared light, as illustrated in FIG. 3a, but reflects most or all visible light, as illustrated in FIG. 3b. In some embodiments, the partial mirror may be a cold mirror. In an embodiment, the cold mirror may be an edge shaped filter configured to transmit light in the infrared range and reflect light in a band below the infrared range, which includes visible light. In additional embodiments, the partial mirror 110 may include a band pass filter configured to transmit a specific wavelength of light (e.g., 1000-1100 nm) and reflect other wavelengths of light. In still additional embodiments, the partial mirror 110 may have an anti-reflection coating on one side of the partial mirror 110 that prevents reflection of infrared or other wavelength bands of light.

After passing through the partial mirror 110, at least a portion of the sample beam 104 is further passed to a sample 111, e.g., an eye, for scanning. The sample beam 104 is then reflected off of the sample 111 and travels back via the sample path to a detector (not depicted). Once the sample beam 104 reaches the detector, the sample beam 104 is detected and processed.

Alternatively, if at least another portion of the sample beam 104 is reflected off of a switching mirror 106, the sample beam 104 may be reflected to a mirror 108 and through a second lens 113. In an embodiment, the second lens 113 is a converging lens that is configured to refract the sample beam 104 toward a focal point that may allow the sample beam 104 to scan the sample 111, e.g., an eye. According to such an embodiment, the retina of an eye may be scanned using the converging sample beam 104. In alternative embodiments, other lenses may be used in place of a converging lens according to the desired type of imaging to be performed on the sample 111. Before reaching the sample 111, the sample beam 104 passes through a second aperture 109 and a partial mirror 110. In some embodiments, the partial mirror 110 may be one continuous mirror from first aperture 107 to the second aperture 109 or it may be two separate partial mirrors. Additionally, there may also be reference markers on the partial mirror 110 that assist in the alignment of a sample, e.g., a patient's eye. The sample beam 104 then reflects off of the sample 111 and passes back through the same sample path that it followed on its way to the sample to a detector where the beam is detected and further processed.

In some embodiments, an eye cup 120 may be disposed around the second scan aperture 109. The eye cup can assist in ensuring that a patient's eye is a correct distance from and location relative to the opening of the second scan aperture 109. In some embodiments, the eye cup 120 may be a hollow cylinder or it may be a hollow-truncated cone with varying degrees of ligand cone angles. The eye cup 120 may be made out of a variety of materials that are rigid, yet comfortable for the patient, including but not limited to aluminum, rubber, plastic, or a combination thereof. In yet other embodiments, the eye cup may be removable and/or disposable in order to ensure hygienic practices.

The distance between the second lens 113 and the partial mirror 110 can change depending on the focal length of the second lens 113 and the depth of the eye cup 120. The angle of incidence 114, or scan angle, in which the sample beam 104 enters the sample 111 may affect the quality and resolution of the scan. However, if the patient is too close to the partial mirror 110, or the eye cup depth is too short, then the patient may not be able to focus on the mirror image of his or her eye (see discussion of FIG. 4 below). Thus, it follows that in alternative embodiments, the size of the aperture openings, the thickness of the partial mirror, the focal length of the converging lens, the distance between the partial mirror and the converging lens, and the depth of the eye cup variables may change and be optimized depending on the specific characteristics of the equipment being used.

The OCT system 100 also includes a fixation light 130. In an embodiment, the fixation light 130 may include a light-emitting diode (LED) or any other suitable light source known to those of skill in the art. The fixation light 130 may be positioned behind the mirror 108 along an optical axis 131, as illustrated in FIG. 1. The fixation light 130 emits a beam of light 131 that travels through the second aperture 109 and is visible to the sample 110. In an embodiment, the fixation light may have a wavelength in a range between red and infrared light such that a portion of the fixation light may be transmitted through a col mirror and be visible to the sample 111. The beam of fixation light 130 may help a patient to correctly position his or her eye relative to the OCT system 100. This helps ensure that the sample beam 104 reaches its correct target (e.g., the retina of an eye) and that the scan angle 114 is maximized for better resolution. In alternative embodiments, the fixation light 130 could be a different source of light, positioned along a plurality of optical axes, or there could be multiple on either aperture. The fixation light 130 may be included in one or both apertures 107, 109.

The OCT system 100 may also include a camera 112. In an embodiment, the camera 112 may be a complementary metal-oxide semiconductor (CMOS) camera, charge-coupled device (CCD) camera or any other suitable camera known to those of skill in the art. The camera 112 may allow for recording, and monitoring of the sample 111 (e.g. a patient's eye) along its positioned optical axis. In alternative embodiments, there may be more than one camera 112 and it may be used to assist in aligning the sample 111 correctly. In yet other embodiments, the camera 112 may be positioned along different optical axes in one, or both, of the apertures 107 and 109.

FIG. 2a illustrates an OCT embodiment 200 where the switching mirror 106 is actuated to change the sample beam's 104 sample path. An actuator 210 is a device in which moves the switching mirror 106 in and out of the sample path. In an embodiment, the actuator 210 may be a linear motor that linearly actuates the switching mirror 106. In other embodiments, the actuator 210 may be an electrically activated solenoid. The actuator 210 may move the mirror into the sample path in order to direct the sample beam 104 towards mirror 108 and into the second aperture 109. Alternatively, actuator 210 may displace the switching mirror 106 out of the sample path so that the sample beam 104 can enter the first aperture 107. In alternative embodiments, actuator 210 may be controlled either manually, electronically, or as part of a computer algorithm and may travel in a linear motion or be pivoted or rotated on an axis.

FIG. 2b illustrates another OCT 201 embodiment where the switching mirror 106 is a polarized beam splitter (PBS). In some embodiments, the PBS may be a dielectric filter type PBS or a birefringent crystal PBS utilizing calcite or wallaston prisms. The polarized beam splitter reflects the portion of the sample beam 104 with a certain polarization and transmits the portion of the sample beam 104 at a different polarization. In an embodiment, the PBS may allow all or most portions of the sample beam 104 that have an electric field parallel to the plane of incidence, also known as P-type polarization 222, to transverse the switching mirror 106 to enter the first aperture 107, and reflect the portions of the sample beam 104 that have polarization perpendicular to the plane of incidence, also known as S-type polarization 221, to the second mirror 108 and into the second aperture 109. In alternative embodiments, the PBS may transmit or reflect alternative portions of the sample beam 104.

In some embodiments, as illustrated in FIG. 2b, there may be a polarizer switch 220. The polarizer switch 220 may be a liquid crystal switch, a magnetic optic crystal switch, a mechanically rotating waveplate (e.g., a quarter or half-waveplate), a mechanically rotating faraday rotator, or any other suitable polarizer switch. In yet other embodiments, the polarizer switch 220 may change the polarization of portions or all of the incoming beam by anywhere from 0 degrees to 90 degrees. Alternatively, the polarizer switch 220 may not change the polarization of portions or all of the incoming beam.

FIGS. 3a and 3b illustrate the properties of the partial mirror 110. The x-axis of FIG. 3a shows the wavelength and the y-axis corresponds to the percentage of transmittance that the partial mirror 110 allows. The partial mirror 110 allows a high percentage of transitivity at longer wavelengths, e.g., infrared light, but has a low percentage of transitivity at shorter wavelengths, e.g., visible light. In alternative embodiments, the transitivity maximum of the partial mirror 110 may be anywhere from 80-100 percent, and the minimum may be in the range of 0 to 20 percent. In another embodiment, the slope of the transitivity line corresponding to the partial mirror 110 may be different and its inflection point 301 may be located at different wavelengths.

FIG. 3b illustrates the reflectivity versus the wavelength of the partial mirror 110. The partial mirror 110 exhibits a high reflectivity percentage in the visible range of light, e.g., shorter wavelengths, and exhibits low reflectivity percentages for infrared light, e.g., light have longer wavelengths. In some embodiments, the reflectivity maximum of the partial mirror 110 may be in the range of 80 to 100 percent, and the minimum may be in the range of 0 to 20 percent. In other embodiments, the inflection point 302 of the reflectivity versus wavelength line unique to partial mirror 110 may be located at different wavelengths. The amount of reflectivity and transitivity at each wavelength may change in accordance with a coating design of the partial mirror, e.g., an anti-reflection coating may be used.

Figure 4:
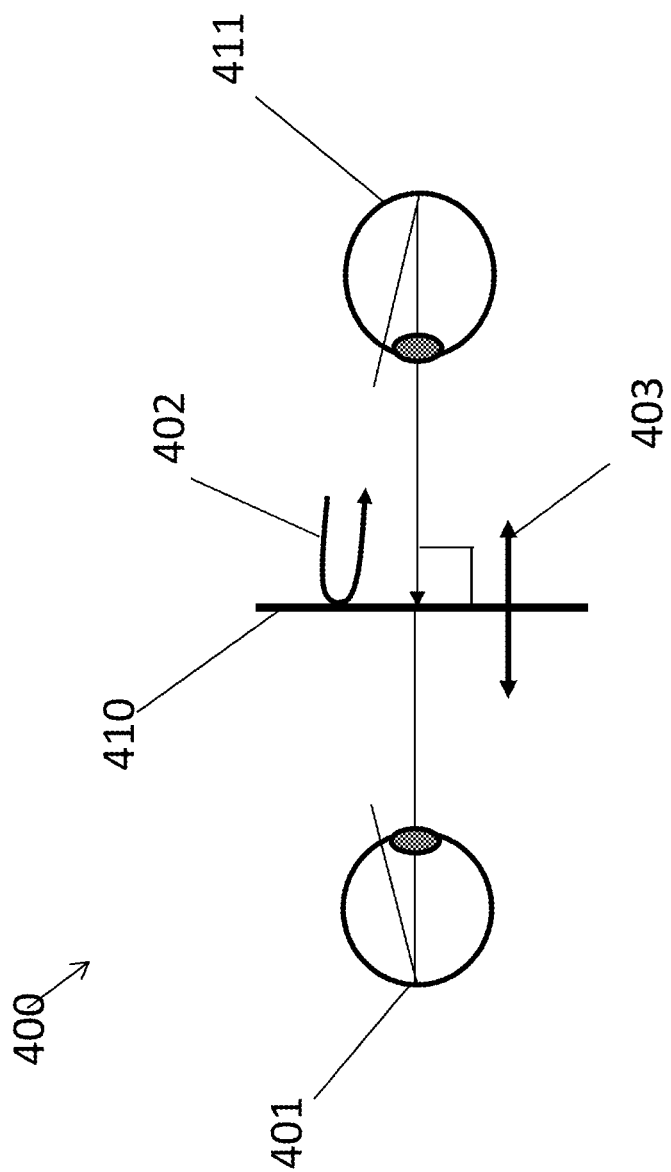
FIG. 4 depicts a side view of a partial mirror in an OCT system in accordance with an illustrative embodiment.

FIG. 4 illustrates a side view 400 of a partial mirror 410 in an OCT system. The partial mirror 410, as explained above, transmits at least most infrared light and reflects at least most visible light. FIG. 4 illustrates an embodiment where a patient's eye 411 is aligned with the partial mirror 410 and the OCT signal 403 passes through the partial mirror 410 from the OCT system to the subject's eye 411. FIG. 4 further illustrates an embodiment where the visible light 402 is reflected off of the partial mirror 410 and returns to the patient's eye 411, and as a result, the patient sees a mirror image 401 of his or her eye. In such an embodiment, a visual axis of the eye is aligned perpendicular to the partial mirror 410 and parallel to an optical axis of the aperture into which the patient is looking. In some embodiments, the OCT signal 403 is the sample beam 104.

In yet other embodiments, fixation points are located on the partial mirror 410 that are configured to ensure that the patient's eye 411 is correctly situated, which may eliminate the need for mechanical alignment of the OCT system. Correct positioning of the eye 411 may include positioning of the eye 411 along an axis that is parallel to and centered within the optical axis of the aperture such that the eye 411 is not tilted relative to the optical axis. In another embodiment, there may be more elements such as lenses, fixation lights, cameras, or eye cups in the embodiment to assist with alignment. In some embodiments, the partial mirror 410 may be the same as partial mirror 410.

Figure 5:
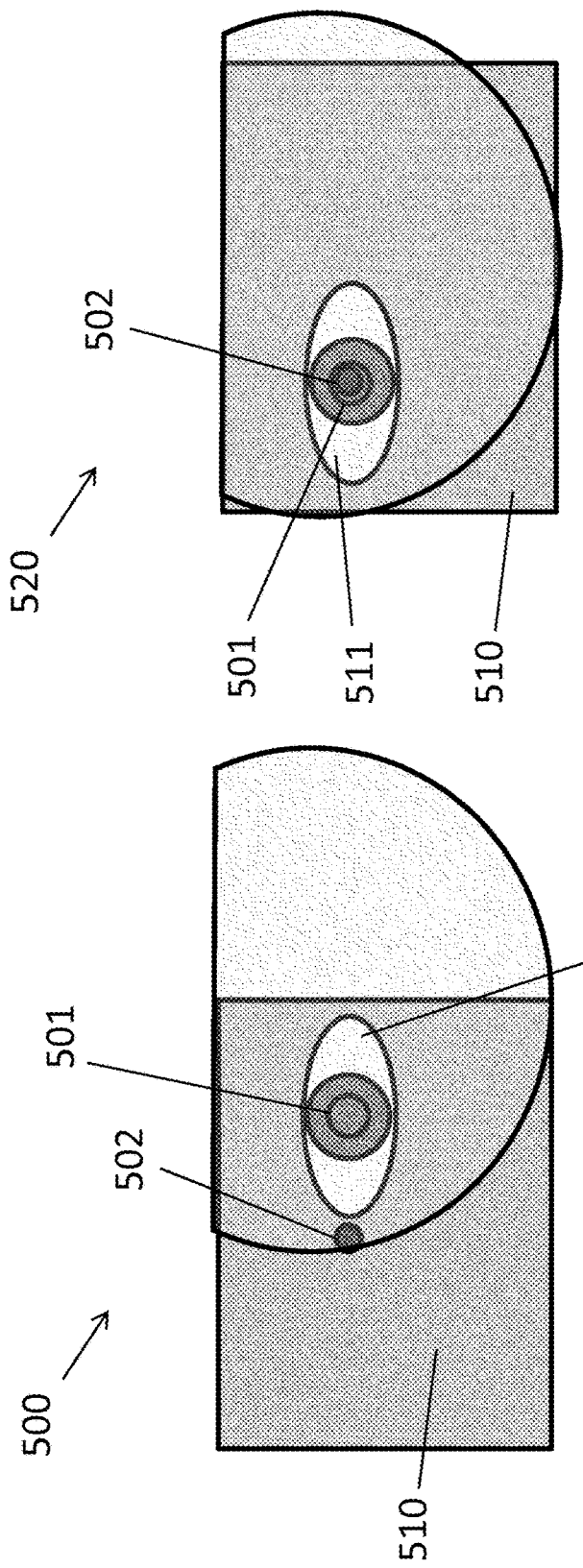
FIG. 5a depicts an eye that is misaligned to the OCT system in accordance with an illustrative embodiment.
FIG. 5b depicts an eye that is aligned to the OCT system in accordance with an illustrative embodiment.

FIGS. 5a and 5b illustrate embodiments 500 and 520 of a partial mirror 510 used to align a patient's eye 511. Illustrated in both embodiments are a patient's eye 511, a patient's pupil 501, and a fixation point 502 on the partial mirror 510. In alternative embodiments, the fixation point 502 may be from a light (e.g., fixation light 130 from FIG. 1) emitted from behind, or in front, of the partial mirror 110. The fixation light may be desirable for situations in which a patient is too close to the partial mirror 110 or an eye cup depth is too short and the patient may not be able to focus on a mirror image of his or her eye.

In other embodiments, the fixation point 502 may be a marking on the partial mirror 510 itself. In the embodiment 500, the patient's eye 511 can see the fixation point 502 and a mirror image of his or her eye on the partial mirror 511. FIG. 5a illustrates the patient's eye 511 in a position that is improperly aligned with the fixation point 502. Whereas FIG. 5b illustrates the patient's eye 511 in a position such that the patient's eye 511 is properly aligned with the fixation point 502. For example, the pupil 501 of the patient's eye 511 is aligned with the fixation point 502. Through proper alignment of the pupil 501 with the fixation point 502, as illustrated in FIG. 5b, the patient's eye 511 is aligned with the OCT system 100, which may allow for less mechanical movement of the OCT system and more accurate OCT scans of the eye. In alternative embodiments, there may be one or more fixation points 502 that can be aligned to different parts of the patient's eye.

Figure 6:
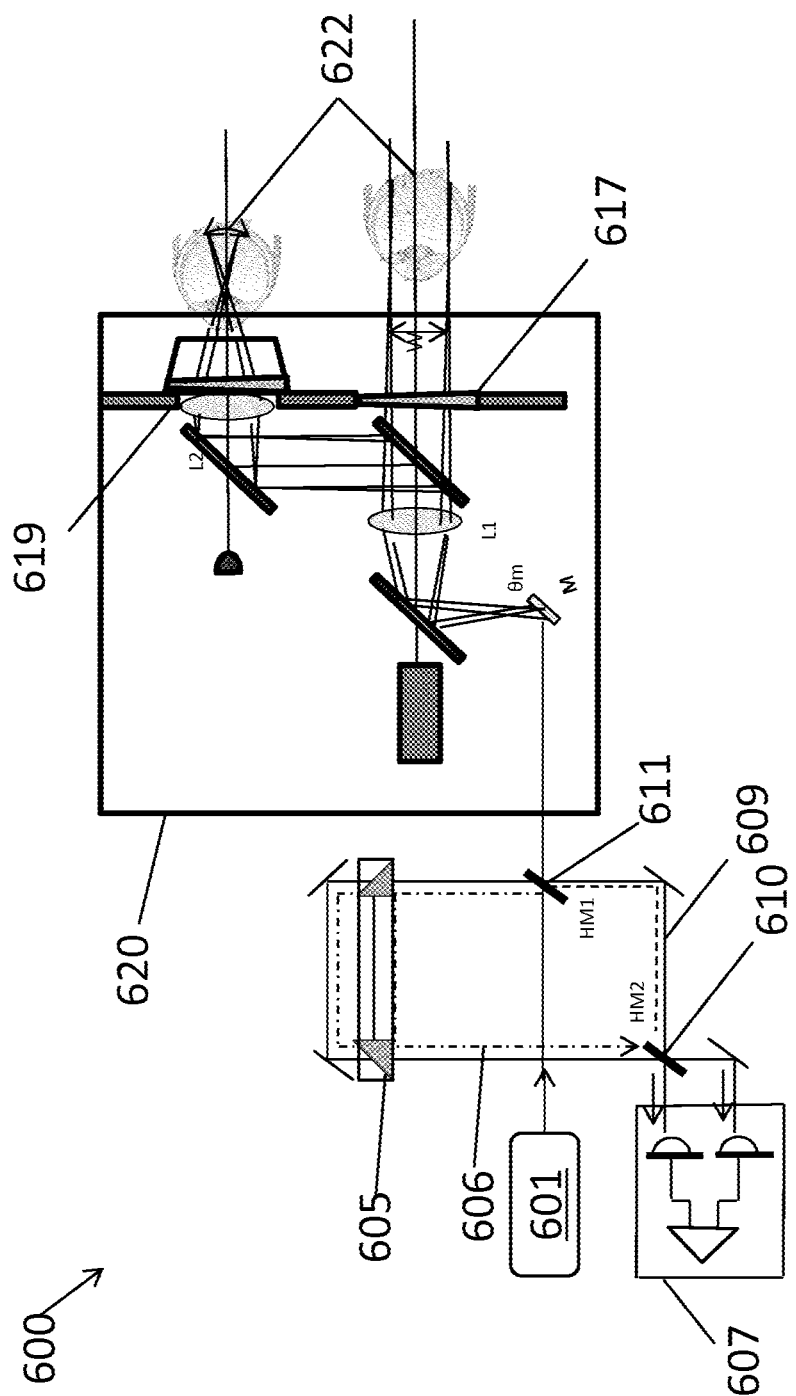
FIG. 6 depicts an OCT system including a free-space optics interferometer in accordance with an illustrative embodiment.

FIG. 6 illustrates an embodiment of an OCT system 600 that is operated by a free-space optics based interferometer. In this illustrative embodiment, the OCT system 600 includes a swept source 601. The swept source 601 is configured to emit a beam into the interferometer 609. The interferometer 609 includes a reference path 606 and a sample path. The beam from the swept source 601 impinges upon a half mirror 611 that reflects some of the beam into the reference path 606, but allows some of the beam to continue into a mirror and lens embodiment 620.

The reference path 606 should be about the same distance as the sample path in order to obtain accurate imaging. Accordingly, the reference path 605 may change depending on which sample path and aperture in the OCT system is being utilized. That is, when using a second aperture 619, the reference path may need to be longer because of the longer sample path. Whereas, when a first aperture 617 is being utilized the reference path may need to be shorter because the sample path is shorter. OCT system 600 further includes a path length switch 605 that allows for adjustment of the reference path accordingly. In alternative embodiments, the reference path may be pre-adjusted or predetermined according to which aperture is going to be used.

In the embodiment of FIG. 6, the beam from the reference path 606 and the beam that is returned from the patient's eye 622 impinge upon a half mirror 610 that creates an interference signal between the beam from the reference path 606 and the returned beam and directs the interference signal into one side of a balanced photo-detector 607 and allows some of the beam to reach another mirror which reflects the beam into the other side of the balanced photo-detector 607. The beams are then detected by the balanced photo-detector 607 and an output image is created based on a Fourier Transform of the detected interference.

Figure 7:
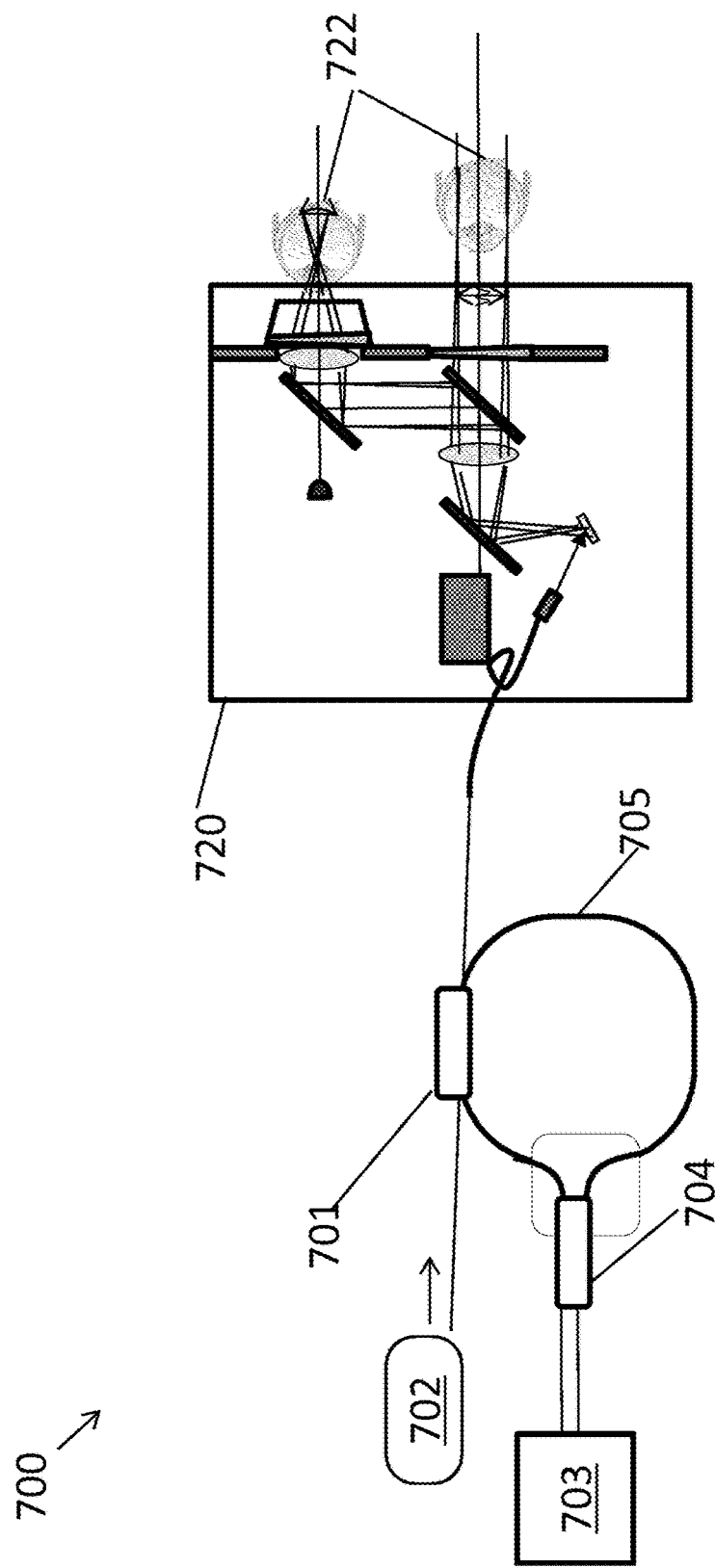
FIG. 7 depicts an OCT system including a fiber based interferometer in accordance with an illustrative embodiment.

FIG. 7 illustrates an embodiment of an OCT system 700 configured to be operated by a fiber based interferometer. The embodiment 700 utilizes a swept source 702 that emits a beam into a first fiber coupler 701. The first fiber coupler 701 splits the beam and creates a reference path beam and a sample path beam that enters into a mirror and lens embodiment 720. The sample path beam returns after impinging upon a patient's eye 722 and follows the reference path 705 to a second fiber coupler 704. The second fiber coupler 704 then recombines the reference path beam and the sample path beam and creates an interference signal which is transmitted into a balanced photo-detector 703 to be detected and processed.

Figure 8:
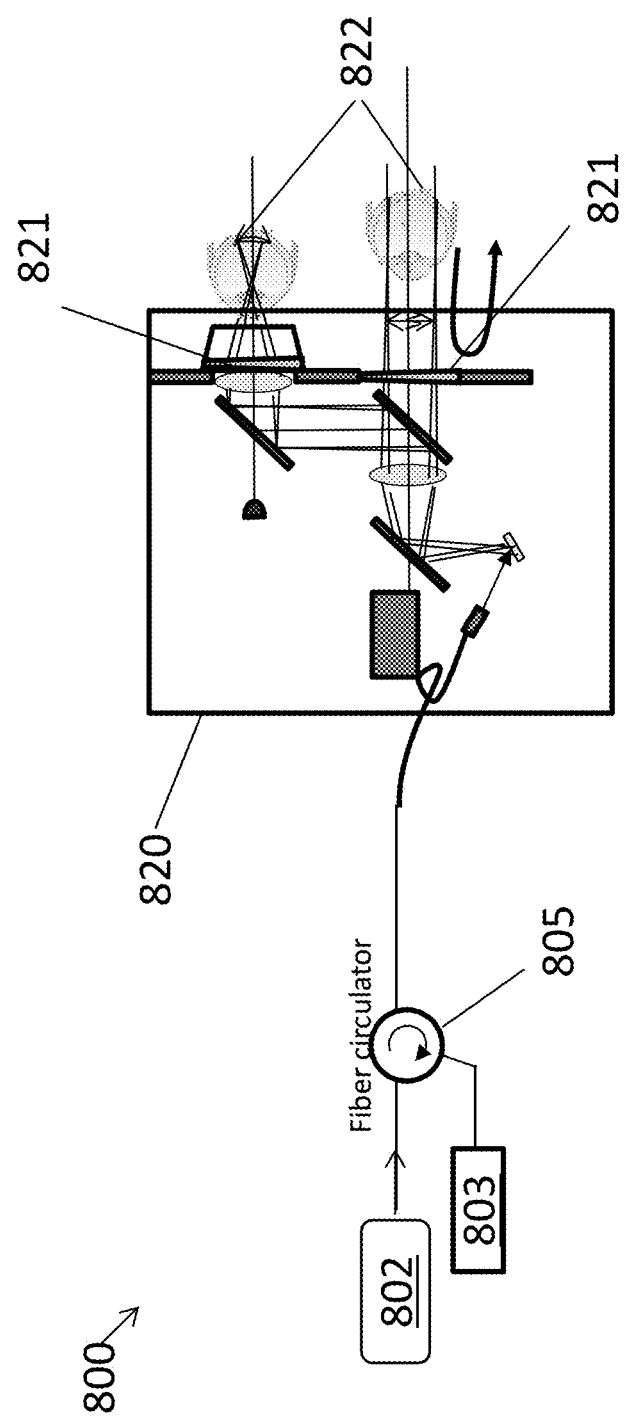
FIG. 8 depicts an OCT system including a Fizeau based interferometer in accordance with an illustrative embodiment.

FIG. 8 illustrates an embodiment of an OCT system 800 that is operated by Fizeau based interferometer. The Fizeau based interferometer utilizes a swept source 802 that emits a beam into a fiber circulator 805. The fiber circulator 805 passes the beam into the OCT system where it travels to a partial mirror 821 and a patient's eye 822. The partial mirror 821 transmits most of the beam, which in an embodiment 800 includes primarily infrared light, but a small amount of the beam is reflected back. In some embodiments, the small portion of the beam that is reflected is in the range of 0 to 10 percent of the impinging sample beam 104.

Accordingly, the portion of the beam that is reflected off the partial mirror 821 is considered as the reference path beam, and the portion that is reflected off of the patient's eye 822 is considered as the sample path beam. The two beams are then reflected back to create an interference signal which is passed to the fiber circulator 805. The fiber circulator 805 transmits the beams into a detector 803 for processing.

Figure 9:
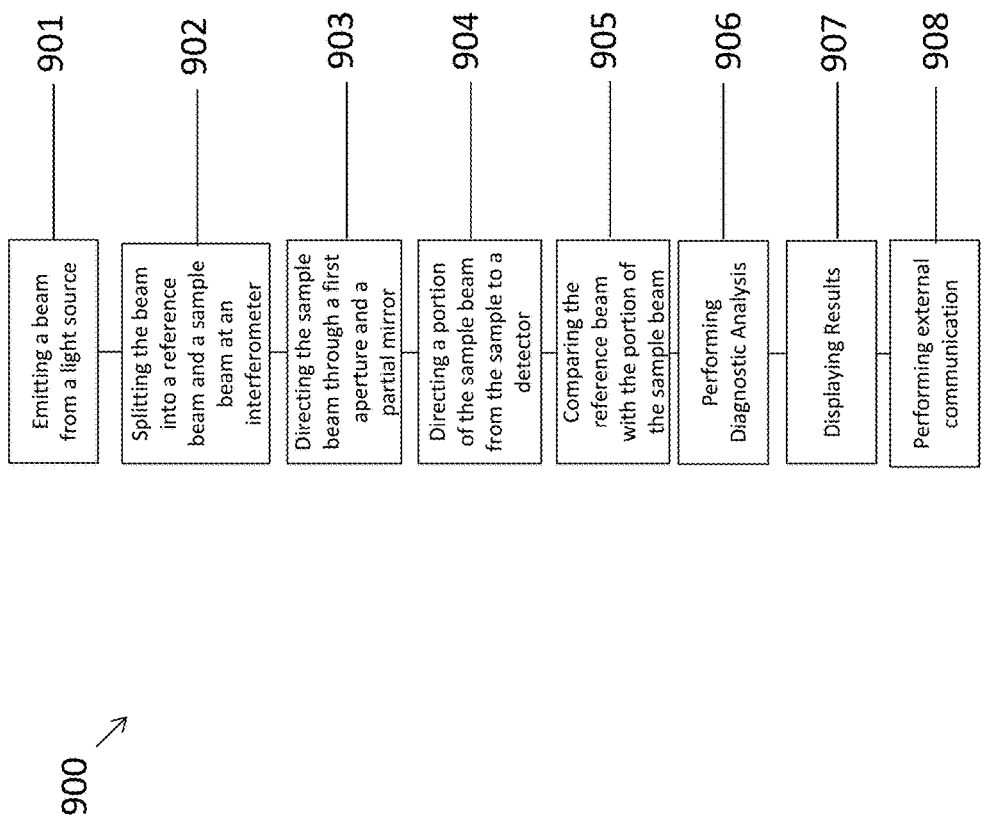
FIG. 9 depicts a method of using an OCT system in accordance with an illustrative embodiment.

FIG. 9 illustrates a method 900 of operation of an OCT system in accordance with an illustrative embodiment. In an operation 901, a beam is emitted from a light source. In an operation 902, the beam is split into a reference beam and a sample beam at an interferometer. In an embodiment, the interferometer may be a free-space optics based interferometer, a fiber based interferometer, a Fizeau based interferometer, or other types of interferometers. In an embodiment, a swept light source may emit the beam into the interferometer and then into a mirror and lens system.

In an operation 903, a mirror system directs the sample beam through a first aperture and through a partial mirror disposed over at least a portion of the first aperture. The mirror system may include one or more mirrors, lenses, or other optical routing components for passing the sample beam to the first aperture. In an embodiment, the mirror system may include a scan mirror that reflects the sample beam to a first mirror that is further configured to reflect the sample beam towards a lens associated with the first aperture. The partial mirror is designed to pass at least a portion of the light of the sample beam. In another embodiment, there may be a partial mirror disposed over at least a portion of a second aperture. Furthermore, the mirror system may include a switching mirror that can selectively direct the sample beam towards the first aperture or the second aperture. In some embodiments, the switching mirror may be actuated into and out of a sample path to selectively direct the sample beam toward the first aperture or the second aperture. For example, when the mirror is actuated into the sample path the beam is directed towards a second aperture, and when it is actuated out of the sample path the beam enters the first aperture. In other embodiments, the switching mirror may be a polarized beam splitter capable of directing light having a first polarization direction towards the first aperture and light having a second polarization towards the second aperture.

In an operation 904, the sample beam is reflected off of the sample and directed to a detector via the mirror system. In an operation 905, the detector compares the reference beam with the portion of the sample beam reflected from the sample to generate a measurement signal. In an operation 906, the system makes a diagnostic analysis. In an operation 907, the results of the diagnostic analysis are displayed on a screen. In an operation 908, the results of the diagnostic analysis and/or the measurements may be externally communicated. For example, a patient or healthcare provider may transmit the information and discuss the diagnostic results.

Figure 10:
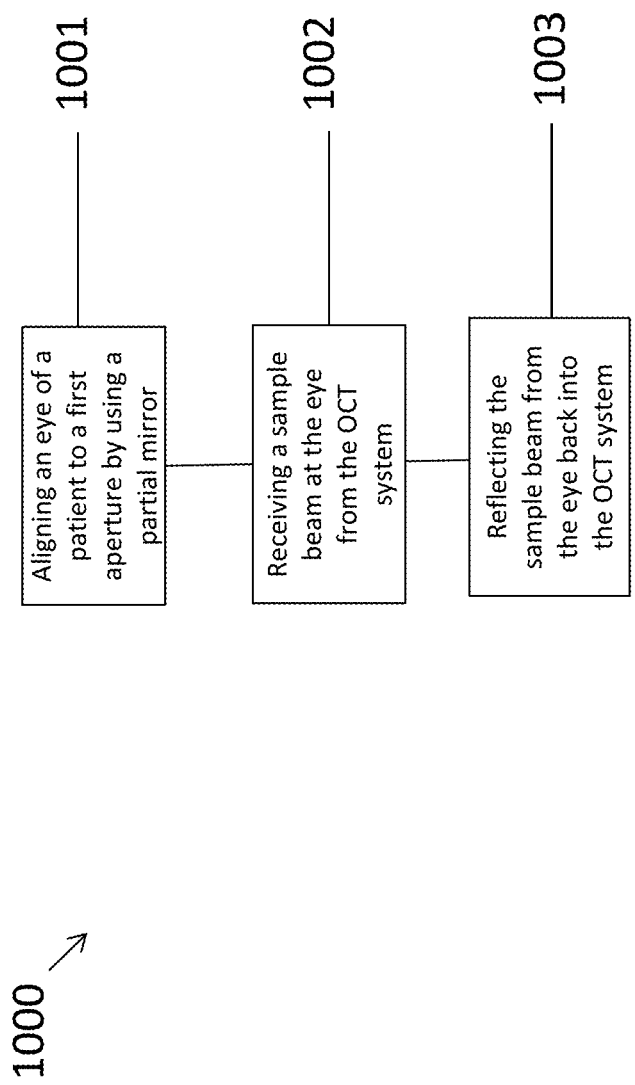
FIG. 10 depicts a method of using an OCT system in accordance with an illustrative embodiment.

FIG. 10 illustrates a method 1000 of operation of an OCT system in accordance with an illustrative embodiment. In an operation 1001, a subject or patient looks at a partial mirror disposed over at least a portion of a first aperture of an OCT system and aligns his or her eye with the OCT system using the partial mirror. In an embodiment, additional alignment aids (other than just the partial mirror) may be used by the OCT system to facilitate alignment of the eye. For example, fixation marks on the partial mirror on an optical axis, a fixation light emitted through the partial mirror on an optical axis, an eye cup, and or a camera display may be further used to facilitate alignment.

In an operation 1002, the patient's eye receives a sample beam that travels through the first aperture of the OCT system. In operation 1003, the sample beam is reflected from the eye back through the first aperture of the OCT system where it may be detected and processed. In alternative embodiments, the patient may move to a second aperture and repeat the alignment steps. The patient's eye may receive a second sample beam from the second aperture and his or her eye may reflect the sample beam back through the second aperture of the OCT system to be detected.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Additional embodiments may be set forth in the following claims.

What is claimed is:

1. An optical coherence tomography (OCT) system comprising:
    a light source configured to emit a light beam;
    an interferometer configured to split the light beam into a reference beam and a sample beam;
    a mirror system configured to route the sample beam to at least one of a first aperture or a second aperture for imaging of a sample, wherein the mirror system further comprises a switching mirror configured to selectively direct at least a portion of the sample beam into the first aperture or direct at least a portion of the sample beam towards the second aperture;
    a first partial mirror positioned across at least a portion of the first aperture, wherein the partial mirror is configured to transmit light within a first wavelength range and reflect light within a second wavelength range; and
    a detector configured to detect a signal based on an interference between the reference beam and a portion of the sample beam reflected from the sample.

2. The system of claim 1, further comprising a second partial mirror positioned across at least a portion of the second aperture, wherein the second partial mirror is configured to transmit light within the first wavelength range and reflect light within the second wavelength range.

3. The system of claim 1, wherein the first partial mirror is positioned across at least a portion of each of the first and second apertures.

4. The system of claim 1, wherein the switching mirror comprises a polarized beam splitter configured to direct light having a first polarization direction toward the first aperture and to direct light having a second polarization direction toward the second aperture.

5. The system of claim 4, wherein the second polarization direction is perpendicular to the first polarization direction.

6. The system of claim 1, further comprising an actuator configured to selectively move the switching mirror into and out of a sample path to selectively direct the sample beam toward the first aperture or the second aperture.

7. The system of claim 1, further comprising a fixation mark etched on the partial mirror, wherein the fixation mark is aligned with an optical axis along which the sample beam is configured to pass through the first aperture.

8. The system of claim 1, further comprising a fixation light positioned behind the partial mirror, wherein the fixation light is configured to emit a beam of light along an optical axis along which the sample beam is configured to pass through the first aperture.

9. The system of claim 1, further comprising an eye cup disposed over the first aperture.

10. The system of claim 1, wherein the first partial mirror comprises an anti-reflection coating.

11. The system of claim 1, further comprising a display integrated into the first partial mirror, wherein the display is configured to present measured diagnostic information based on the detected signal.

12. An optical coherence tomography (OCT) system comprising:
   a light source configured to emit a light beam;
   an interferometer configured to split the light beam into a reference beam and a sample beam;
   a mirror system configured to route the sample beam to a first aperture for imaging of a sample;
   a first partial mirror positioned across at least a portion of the first aperture, wherein the partial mirror is configured to transmit light within a first wavelength range and reflect light within a second wavelength range;
   a detector configured to detect a signal based on an interference between the reference beam and a portion of the sample beam reflected from the sample;
   a distance sensor configured to sense a distance of the sample from the first aperture; and
   an alarm configured to indicate when the distance is within a range suitable for conducting a measurement with the OCT system.

13. A method of using an optical coherence tomography (OCT) system comprising:
   emitting a beam from a light source;
   splitting the beam into a reference beam and a sample beam at an interferometer;
   directing, via a mirror system, the sample beam through a first aperture and through a partial mirror disposed over at least a portion of the first aperture, wherein the partial mirror is configured to transmit light within a first wavelength range and reflect light within a second wavelength range, and wherein the mirror system comprises a switching mirror configured to selectively direct the sample beam toward the first aperture or toward a second aperture;
   directing, via the mirror system, a portion of the sample beam reflected from a sample to a detector;
   comparing, via the detector, the reference beam with the portion of the sample beam reflected from the sample to generate a measurement signal corresponding to the sample.

14. The method of claim 13, wherein the switching mirror comprises a polarized beam splitter, the method further comprising directing, by the polarized beam splitter, the sample beam toward either the first aperture or the second aperture based on a polarization direction of the sample beam, wherein light having a first polarization direction is directed toward the first aperture and light having a second polarization is directed toward the second aperture, and wherein the first polarization direction is perpendicular to the second polarization direction.

15. The method of claim 13, further comprising moving, via an actuator, the switching mirror into and out of a path of the sample beam, wherein the switching mirror is configured to direct light to the second aperture when the switching mirror is located within the path of the sample beam, and wherein the sample beam passes to the first aperture when the switching mirror is not located within the path of the sample beam.

16. A method of using an optical coherence tomography (OCT) system comprising:
   aligning an eye of a patient with a first aperture using a reflection in a partial mirror disposed over at least a portion of the first aperture, wherein the partial mirror is configured to pass infrared light and reflect visible light;
   aligning the eye with a fixation mark disposed on the partial mirror, wherein the fixation mark is disposed along an optical axis of the sample beam; and
   receiving a sample beam at the eye, wherein the sample beam passes through the first aperture and the partial mirror and is reflected back into the OCT system, and wherein a measurement of the eye is based on the reflected sample beam.

17. The method of claim 16, wherein aligning the eye with the first aperture further comprises aligning the eye with a fixation light emitted through the first aperture, wherein the fixation light is disposed along an optical axis of the sample beam.

* * * * *